US012673215B2

(12) United States Patent
Greenberg et al.

(10) Patent No.: US 12,673,215 B2
(45) Date of Patent: Jul. 7, 2026

(54) SYSTEM FOR APPLICATION OF ALTERNATING MAGNETIC FIELDS TO REDUCE INFECTION

(71) Applicant: SOLENIC MEDICAL, INC., Addison, TX (US)

(72) Inventors: David Greenberg, Coppell, TX (US); John Tepper, Carrollton, TX (US); Rajiv Chopra, Dallas, TX (US)

(73) Assignee: SOLENIC MEDICAL, INC., Addison, TX (US)

( * ) Notice: Subject to any disclaimer, the term of this patent is extended or adjusted under 35 U.S.C. 154(b) by 586 days.

(21) Appl. No.: 18/258,452

(22) PCT Filed: Dec. 20, 2021

(86) PCT No.: PCT/US2021/064285
§ 371 (c)(1),
(2) Date: Jun. 20, 2023

(87) PCT Pub. No.: WO2022/140226
PCT Pub. Date: Jun. 30, 2022

(65) Prior Publication Data
US 2024/0033533 A1      Feb. 1, 2024

Related U.S. Application Data

(60) Provisional application No. 63/129,692, filed on Dec. 23, 2020.

(51) Int. Cl.
*A61N 2/00*          (2006.01)
*A61L 27/04*          (2006.01)
(Continued)

(52) U.S. Cl.
CPC .............. *A61N 2/004* (2013.01); *A61L 27/04* (2013.01); *A61L 27/50* (2013.01); *A61N 2/02* (2013.01);
(Continued)

(58) Field of Classification Search
CPC ........... A61N 2/004; A61N 2/02; A61L 27/04; A61L 27/50; A61L 2430/24; G06T 7/74;
(Continued)

(56) References Cited

U.S. PATENT DOCUMENTS

| | | |
|---|---|---|
| 4,524,079 A | 6/1985 | Hofmann |
| 4,658,836 A | 4/1987 | Turner |

(Continued)

FOREIGN PATENT DOCUMENTS

| | | |
|---|---|---|
| AU | 746410 B2 | 5/2002 |
| AU | 2014364214 B2 | 12/2014 |

(Continued)

OTHER PUBLICATIONS

Cheng et al., "Remote acoustic sensing as a safety mechanism during exposure of metal implants to alternating magnetic fields," Plos One, May 10, 2018, 20 pages.
(Continued)

*Primary Examiner* — Bo Joseph Peng
(74) *Attorney, Agent, or Firm* — Trop, Pruner & Hu, P.C.

(57) ABSTRACT

An embodiment includes: (1) determining a first orientation of first and second portions of a first image with respect to one another, wherein the first portion depicts a first metallic implant and the second portion depicts a first coil, wherein the first orientation is based on: (a) a first distance between the first and second portions with respect to one another, and (b) a first direction between the first and second portions with respect to one another; (2) select a first target orientation for the first metallic implant and the first coil with
(Continued)

200

Manually position transducer coil on patient ("best guess"). 201

Image coil (which has fiducials) together with implant on patient. 202

Import image into coordinate matrix in AMF processor (which is part of AMF equipment stack). 203

Verify coil model/type by examining built-in coil fiducials. 204

Compare imaged implant with implants in the implant library to determine actual implant model. 205

Calculate difference between actual implant location in coordinate matrix with ideal location from simulation library (which includes model of verified transducer coil and implant image). 206

Calculate movement needed in, for example, rectilinear (x, y, z) or polar (r, theta, phi) coordinates to get to ideal location of transducer coil. 207

Manually reposition transducer coil per instructions given on AMF unit screen. 208

Automatically reposition coil using outputs generated by AMF unit. 209 respect to one another from a library of target orientations between implants and coils; (3) determine a first difference between the first orientation and the first target orientation; and (4) output first reorientation instructions via the at least one I/O port in response to determining the first difference between the first orientation and the first target orientation.

23 Claims, 5 Drawing Sheets

(51) Int. Cl.

| | |
|---|---|
| *A61L 27/50* | (2006.01) |
| *A61N 2/02* | (2006.01) |
| *G06T 7/73* | (2017.01) |
| *G06V 10/75* | (2022.01) |
| *G16H 30/40* | (2018.01) |

(52) U.S. Cl.
CPC .............. *G06T 7/74* (2017.01); *G06V 10/751* (2022.01); *G16H 30/40* (2018.01); *A61L 2430/24* (2013.01); *G06T 2207/20092* (2013.01); *G06T 2207/30004* (2013.01); *G06T 2207/30204* (2013.01); *G06V 2201/03* (2022.01)

(58) Field of Classification Search
CPC . G06T 2207/20092; G06T 2207/30004; G06T 2207/30204; G06V 10/751; G06V 2201/03; G06V 10/242; G06V 10/761; G16H 30/40; A61B 5/062
See application file for complete search history.

(56) References Cited

U.S. PATENT DOCUMENTS

| | | | |
|---|---|---|---|
| 4,945,912 A | 8/1990 | Langberg | |
| 5,070,737 A | 12/1991 | Reilly | |
| 5,254,117 A | 10/1993 | Rigby et al. | |
| 5,312,813 A | 5/1994 | Costerton et al. | |
| 5,427,846 A | 6/1995 | McGaffigan | |
| 5,462,644 A | 10/1995 | Woodson | |
| 5,468,210 A | 11/1995 | Matsui et al. | |
| 5,720,775 A | 2/1998 | Larnard | |
| 5,729,129 A | 3/1998 | Acker | |
| 5,764,052 A | 6/1998 | Renger | |
| 5,827,269 A | 10/1998 | Saadat | |
| 5,997,812 A | 12/1999 | Burnham et al. | |
| 6,004,438 A | 12/1999 | Woodson | |
| 6,128,174 A * | 10/2000 | Ritter ....................... A61N 2/02 |
| | | | 361/143 |
| 6,157,853 A | 12/2000 | Blume et al. | |
| 6,206,835 B1 | 3/2001 | Spillman, Jr. et al. | |
| 6,229,126 B1 | 5/2001 | Ulrich et al. | |
| 6,238,421 B1 | 5/2001 | Günther et al. | |
| 6,282,444 B1 | 8/2001 | Kroll et al. | |
| 6,337,627 B1 | 1/2002 | Von Gutfeld et al. | |
| 6,423,953 B1 | 7/2002 | Johnson, Jr. et al. | |
| 6,599,234 B1 | 7/2003 | Gray et al. | |
| 6,618,612 B1 | 9/2003 | Acker et al. | |
| 6,786,904 B2 | 9/2004 | Doscher et al. | |
| 6,802,857 B1 | 10/2004 | Walsh et al. | |
| 6,808,535 B1 | 10/2004 | Jordan | |
| 6,850,803 B1 | 2/2005 | Jimenez et al. | |
| 6,916,630 B2 | 7/2005 | Sofer | |
| 7,010,338 B2 | 3/2006 | Ritter et al. | |
| 7,017,601 B2 | 3/2006 | Soga et al. | |
| 7,038,450 B2 | 5/2006 | Romalis et al. | |
| 7,174,217 B2 | 2/2007 | Rioux et al. | |
| 7,462,959 B2 | 12/2008 | Shinohira et al. | |
| 7,729,778 B2 | 6/2010 | Eggers et al. | |
| 7,731,648 B2 | 6/2010 | Ivkov | |
| 7,744,604 B2 | 6/2010 | Maitland et al. | |
| 7,783,348 B2 | 8/2010 | Gill et al. | |
| 7,918,883 B2 | 4/2011 | Weber | |
| 7,951,061 B2 | 5/2011 | Foreman et al. | |
| 7,967,839 B2 | 6/2011 | Flock et al. | |
| 8,075,734 B2 | 12/2011 | Sorensen et al. | |
| 8,315,700 B2 | 11/2012 | Citron et al. | |
| 8,362,777 B2 | 1/2013 | Eberlein et al. | |
| 8,366,652 B2 | 2/2013 | Dacey, Jr. et al. | |
| 8,373,316 B2 | 2/2013 | Beatty et al. | |
| 8,515,524 B2 | 8/2013 | Furuzono et al. | |
| 8,565,892 B2 | 10/2013 | Nayfach-Battilana | |
| 8,620,431 B2 | 12/2013 | Fuller et al. | |
| 8,644,907 B2 * | 2/2014 | Hartmann .............. A61B 34/20 |
| | | | 600/424 |
| 8,736,266 B2 | 5/2014 | Sakakura | |
| 8,805,536 B2 | 8/2014 | Li et al. | |
| 8,891,847 B2 | 11/2014 | Helm et al. | |
| 9,005,263 B2 | 4/2015 | Boyden et al. | |
| 9,039,697 B2 | 5/2015 | Lischinsky et al. | |
| 9,039,764 B2 | 5/2015 | Gilbert | |
| 9,060,761 B2 | 6/2015 | Hastings et al. | |
| 9,078,655 B2 | 7/2015 | Manwaring et al. | |
| 9,220,557 B2 | 12/2015 | Manwaring et al. | |
| 9,240,007 B2 | 1/2016 | Trevino et al. | |
| 9,282,455 B2 | 3/2016 | Aissi et al. | |
| 9,314,321 B2 | 4/2016 | Nemeh et al. | |
| 9,317,661 B2 | 4/2016 | Helm et al. | |
| 9,320,832 B2 | 4/2016 | Joseph et al. | |
| 9,561,066 B2 | 2/2017 | Sharma et al. | |
| 9,592,160 B2 | 3/2017 | Bacon et al. | |
| 9,610,459 B2 | 4/2017 | Burnett et al. | |
| 9,616,142 B2 | 4/2017 | Ehrensberger et al. | |
| 9,636,495 B2 | 5/2017 | Szasz et al. | |
| 9,693,809 B2 | 7/2017 | Schwab | |
| 9,827,035 B2 | 11/2017 | Schwagten et al. | |
| 9,844,679 B2 | 12/2017 | Nayfach-Battilana | |
| 10,149,712 B2 | 12/2018 | Manwaring et al. | |
| 10,220,119 B2 | 3/2019 | Nazarian et al. | |
| 10,362,417 B2 | 7/2019 | Leigh et al. | |
| 10,500,409 B2 | 12/2019 | Petty et al. | |
| 2001/0012912 A1 | 8/2001 | Feucht | |
| 2001/0055802 A1 | 12/2001 | Sofer | |
| 2002/0138134 A1 | 9/2002 | Kim et al. | |
| 2002/0183829 A1 | 12/2002 | Doscher et al. | |
| 2003/0132144 A1 | 7/2003 | Herbert-Guillou et al. | |
| 2003/0139739 A1 | 7/2003 | Doscher et al. | |
| 2003/0139787 A1 | 7/2003 | Eggers et al. | |
| 2004/0093036 A1 | 5/2004 | Eckerdal et al. | |
| 2004/0098054 A1 | 5/2004 | Eckerdal et al. | |
| 2004/0098055 A1 | 5/2004 | Kroll et al. | |
| 2004/0158310 A1 | 8/2004 | Weber et al. | |
| 2004/0167506 A1 | 8/2004 | Chen | |
| 2004/0210282 A1 | 10/2004 | Flock et al. | |
| 2005/0021088 A1 | 1/2005 | Schuler et al. | |
| 2005/0038376 A1 | 2/2005 | Zumeris et al. | |
| 2005/0058570 A1 | 3/2005 | Raffaele | |
| 2005/0261763 A1 | 11/2005 | Wang et al. | |
| 2006/0142748 A1 | 6/2006 | Foreman et al. | |
| 2007/0099889 A1 | 5/2007 | Royt | |
| 2007/0112344 A1 | 5/2007 | Keilman | |
| 2007/0213645 A1 | 9/2007 | Zumeris et al. | |
| 2008/0319247 A1 | 12/2008 | Forbes et al. | |
| 2009/0216113 A1 | 8/2009 | Meier et al. | |
| 2009/0299437 A1 | 12/2009 | Zimmerling | |
| 2010/0074932 A1 | 3/2010 | Talsma | |
| 2010/0204802 A1 | 8/2010 | Wilson et al. | |
| 2010/0233021 A1 | 9/2010 | Sliwa et al. | |
| 2010/0256607 A1 | 10/2010 | Burnett | |
| 2011/0105825 A1 | 5/2011 | Nayfach-Battilana | |
| 2011/0152750 A1 | 6/2011 | Dacy, Jr. et al. | |
| 2011/0160515 A1 | 6/2011 | Feucht et al. | |
| 2011/0160643 A1 | 6/2011 | Dacy, Jr. et al. | |
| 2011/0251687 A1 | 10/2011 | Prescott | |
| 2012/0101363 A1 | 4/2012 | Gordon et al. | |
| 2013/0188848 A1 | 7/2013 | Helm et al. | |
| 2013/0253387 A1 | 9/2013 | Bonutti et al. | |
| 2014/0005522 A1 * | 1/2014 | Zurovcik .......... A61B 10/0233 |
| | | | 600/12 |
| 2014/0031785 A1 | 1/2014 | Schwagten et al. | |

(56) References Cited

U.S. PATENT DOCUMENTS

| | | | |
|---|---|---|---|
| 2014/0172049 A1 | 6/2014 | Nayfach-Battilana | |
| 2015/0073491 A1 | 3/2015 | Ehrensberger et al. | |
| 2015/0076000 A1 | 3/2015 | Ehrensberger et al. | |
| 2015/0078647 A1 | 3/2015 | Helm et al. | |
| 2015/0157872 A1 | 6/2015 | Vishwanathan et al. | |
| 2015/0265316 A1 | 9/2015 | Schwab | |
| 2015/0359946 A1 | 12/2015 | Dehnad et al. | |
| 2016/0015320 A1 | 1/2016 | Gilbert | |
| 2016/0184002 A1 | 6/2016 | Yang et al. | |
| 2016/0339239 A1* | 11/2016 | Yoo | A61N 1/0456 |
| 2016/0345858 A1 | 12/2016 | Tromberg et al. | |
| 2017/0000918 A1 | 1/2017 | Ehrensberger et al. | |
| 2017/0050040 A1 | 2/2017 | Trembly | |
| 2017/0239473 A1 | 8/2017 | Smyth et al. | |
| 2017/0258526 A1 | 9/2017 | Lang | |
| 2017/0287625 A1 | 10/2017 | Ito et al. | |
| 2017/0312031 A1 | 11/2017 | Amanatullah et al. | |
| 2018/0021463 A1 | 1/2018 | Osinski et al. | |
| 2018/0078329 A1* | 3/2018 | Hansen | H02J 50/90 |
| 2018/0125366 A1 | 5/2018 | Lucey et al. | |
| 2018/0153607 A1* | 6/2018 | Van Langenhove | A61N 1/406 |
| 2018/0271949 A1 | 9/2018 | Struck | |
| 2019/0025040 A1* | 1/2019 | Andreason | A61B 5/062 |
| 2019/0046670 A1 | 2/2019 | Ren et al. | |
| 2019/0059731 A1 | 2/2019 | Peterson | |
| 2019/0105414 A1 | 4/2019 | Ehrensberger et al. | |
| 2019/0159725 A1 | 5/2019 | Chopra et al. | |
| 2019/0175930 A1 | 6/2019 | Weinberg | |
| 2019/0209743 A1 | 7/2019 | Nuxoll et al. | |
| 2019/0247538 A1 | 8/2019 | Dehnad et al. | |
| 2019/0290925 A1 | 9/2019 | Gellman et al. | |
| 2021/0077821 A1 | 3/2021 | De Clerck | |
| 2022/0047733 A1 | 2/2022 | Nelissen et al. | |

FOREIGN PATENT DOCUMENTS

| | | |
|---|---|---|
| CH | 661339 A5 | 7/1983 |
| CN | 102631690 A | 8/2012 |
| CN | 204446661 U | 7/2015 |
| DE | 102014221588 A1 | 10/2014 |
| DE | 102018112298 A1 | 11/2019 |
| EP | 0152963 B2 | 2/1985 |
| EP | 0205851 B1 | 2/1990 |
| EP | 0558297 B1 | 4/1997 |
| EP | 2208506 A1 | 7/2010 |
| EP | 1489985 B1 | 10/2011 |
| EP | 2714186 B1 | 5/2012 |
| EP | 3278839 A1 | 7/2017 |
| EP | 1036574 A1 | 9/2020 |
| GB | 2557900 A | 4/2018 |
| JP | H0663162 A | 3/1994 |
| JP | 2000225176 A | 8/2000 |
| JP | 2014161620 A | 9/2014 |
| KR | 20110052355 A | 5/2011 |
| KR | 20190029680 A | 3/2019 |
| WO | 2002000145 A1 | 1/2002 |
| WO | 2002058785 A1 | 1/2002 |
| WO | 2003059447 A1 | 7/2003 |
| WO | 2008036787 A1 | 3/2008 |
| WO | 2009113397 A1 | 9/2009 |
| WO | 2012141456 A2 | 10/2012 |
| WO | 2012166796 A1 | 12/2012 |
| WO | 2013112452 A1 | 8/2013 |
| WO | 2013159107 A1 | 10/2013 |
| WO | 2013169908 A1 | 11/2013 |
| WO | 2014137454 A1 | 9/2014 |
| WO | 2015148726 A1 | 10/2015 |
| WO | 2016013146 A1 | 1/2016 |
| WO | 2016093319 A1 | 6/2016 |
| WO | 2016157062 A1 | 10/2016 |
| WO | 2018005541 A1 | 1/2018 |
| WO | 2018013935 A1 | 1/2018 |
| WO | 2018034983 A2 | 2/2018 |
| WO | 2018037690 A1 | 3/2018 |
| WO | 2018064150 A1 | 4/2018 |
| WO | 2018235940 A1 | 12/2018 |
| WO | 2019000803 A1 | 1/2019 |
| WO | 2019000804 A1 | 1/2019 |
| WO | 2019000836 A1 | 1/2019 |
| WO | 2019085043 A1 | 5/2019 |
| WO | 2019104213 A1 | 5/2019 |
| WO | 2019147823 A2 | 8/2019 |

OTHER PUBLICATIONS

Jass et al., "The efficacy of antibiotics enhanced by electrical currents against Pseudomonas aeruginosa biofilms," Journal of Antimicrobial Chemotherapy, 38, pp. 987-1000 (1996).

Blenkinsopp et al., "Electrical Enhancement of Biocide Efficacy against Pseudomonas aeruginosa Biofilms," Applied and Environmental Microbiology, vol. 58, No. 11, pp. 3770-3773 ( Nov. 1992).

Van eer Borden et al., "Electric Current-Induced Detachment of Staphylococcus epidermidis Biofilms from Surgical Stainless Steel," Applied and Envionmental Microbiology, vol. 70, No. 11, pp. 6871-6874, Nov. 2004.

Carmen et al., "Treatment of Biofilm Infections on Implants with Low-frequency Ultrasound and Antibiotics," American Journal of Infection Control, 33(2), pp. 78-82, Mar. 2005.

Ricker et al., "Thermal Shock Susceptibility and Regrowth of Pseudomonas aeruginosa Biofilms," International Journal of Hyperthermia, 34(2), pp. 168-176, Mar. 2018.

O'Toole et al., "Thermal mitigation of Pseudomonas aeruginosa biofilms," Biofouling 31(8), pp. 665-675, Sep. 2015.

Alumutairi et al., "Mild magnetic nanoparticle hyperthermia enhances the susceptibility of Staphylococcus aureus biofilm to antibiotics," International Journal of Hyperthermia, 37(1), pp. 66-75, Dec. 2020.

Gerdesmeyer et al., "Antibacterial Effects of Extracorporeal Shock Waves," Ultrasound in Medicine and Biology, vol. 31, No. 1, pp. 115-119, 2005.

Chopra et al. "Employing high-frequency alternating magnetic fields for the non-invasive treatment of prosthetic joint infections," Science Reports, vol. 7, pp. 1-14, 2017.

Ricker et al., "Synergistic effects of heat and antibiotics on Pseudomonas aeruginosa biofilms," Biofouling, vol. 33 (10), pp. 855-866, Nov. 2017.

Pijls et al., "Synergy between induction heating, antibiotics, and N-acetylcysteine eradicates Staphylococcus aureus from biofilm," International Journal of Hyperthermia, vol. 37, No. 1, pp. 130-136, 2020.

Munaweera et al., Temperature-Sensitive Liposomal Ciprofloxacin for the Treatment of Biofilm on Infected Metal Implants using Alternating Magnetic Fields, International Journal of Hyperthermia, vol. 34, No. 2, pp. pp. 189-200, Mar. 2018.

Islam et al., "Global antimicrobial resistance: a complex and dire threat with few definite answers," Tropical Medicine and International Health, vol. 24, No. 6, pp. 658-662, Jun. 2019.

Gas et al., "Cooling effects inside water-cooled inductors for Magnetic Fluid Hyperthermia", 2017 Progress in Applied Electrical Engineering (PAEE), IEEE Xplore, 2017, art. No. 8008997, pp. 1-4, available at: http://dx.doi.org/10.1109/PAEE.2017.8008997.

Kothary et al, "Percutaneous Implantation of Fiducial Markers for Imaging-Guided Radiation Therapy," American Journal of Roentgenology, Apr. 2009, vol. 192, No. 4, pp. 1090-1096.

International Searchign Authority, International Search Report and Written Opinion dated Mar. 16, 2022 in International Patent Application No. PCT/US21/64285 (11 pages).

Hoff et al., "Pose estimation of artificial knee implants in fluoroscopy images using a template matching technique," Proceedings 3rd IEEE Workshop on Applications of Computer Vision, Dec. 2-4, 1996, Sarasota, FL, USA, pp. 181-186.

"Template matching", Wikipedia, downloaded Dec. 9, 2020.

"Pattern recognition", Wikipedia, downloaded Dec. 9, 2020.

"Magnetic Metals & Non-Magnetic Metals With Examples", Fractory, downloaded from https://fractory.com/magnetic-metals-non-magnetic-metals-with-examples/ on Dec. 9, 2020.

"Image analysis", Wikipedia, downloaded Dec. 9, 2020.

"Fiducial marker", Wikipedia, downloaded Dec. 9, 2020.

(56) References Cited

OTHER PUBLICATIONS

"Cartesian coordinates—Math Insight", downloaded from https://mathinsight.org/cartesian_coordinates on Dec. 9, 2020.

European Patent Office, Extended European Search Report dated Sep. 27, 2024 in European Patent Application No. 21911956.7 (9 pages).

Oldhoff et al., "Comparison in clinical performance of surgical guides for mandibular surgery and temporomandibular joint implants fabricated by additive manufacturing techniques", Journal of the Mechanical Behavior of Biomedical Materials, vol. 119, Jul. 2021.

International Searching Authority, International Search Report and Written Opinion dated Mar. 20, 2020 in International Patent Application No. PCT/NL2019/050649 (13 pages).

International Searching Authority, International Preliminary Report on Patentability dated Mar. 23, 2021 in International Patent Application No. PCT/NL2019/050649 (8 pages).

* cited by examiner

100

102

104

106

108

118

116

114

110

112

200

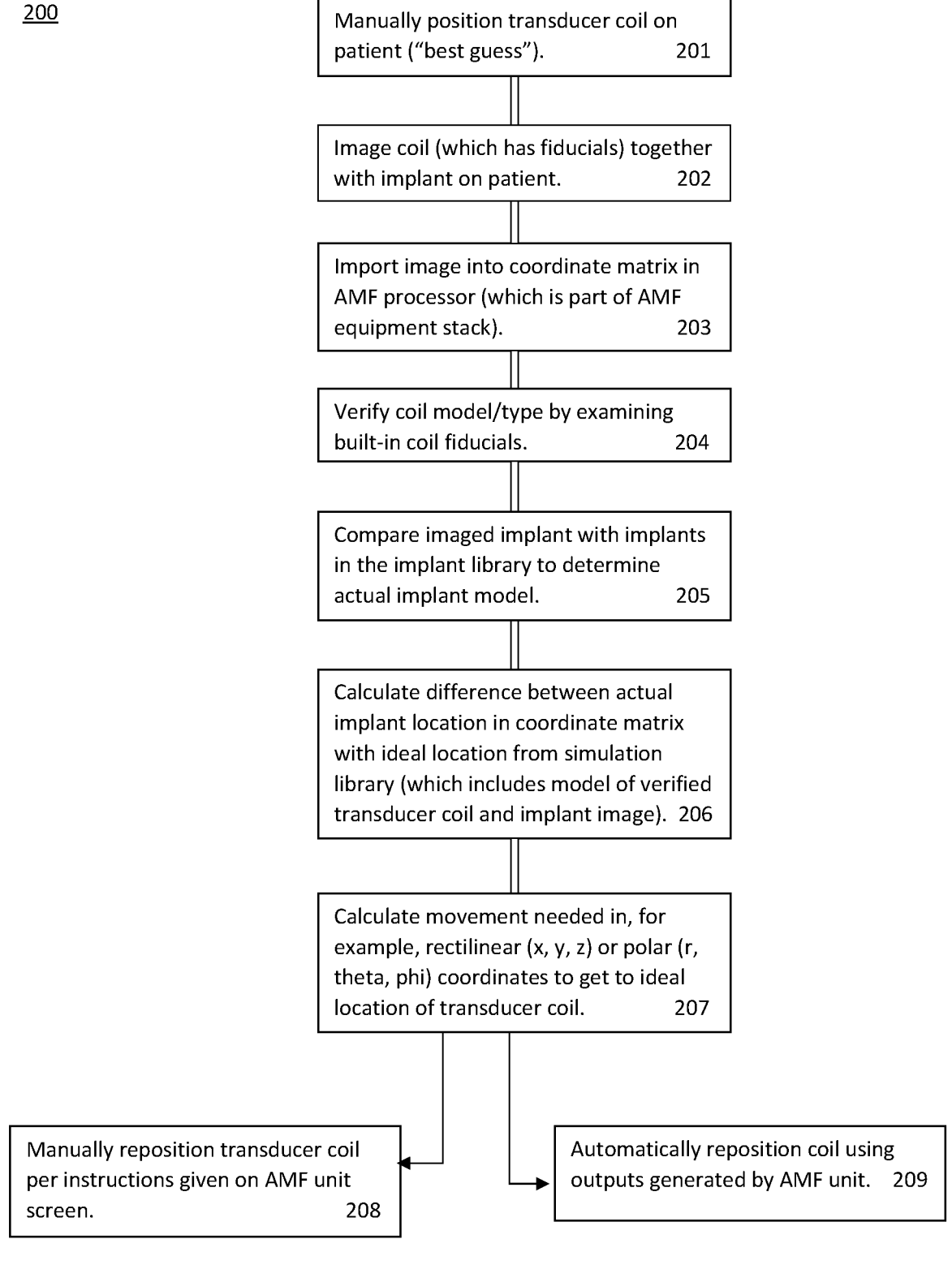

Manually position transducer coil on patient ("best guess").            201

Image coil (which has fiducials) together with implant on patient.            202

Import image into coordinate matrix in AMF processor (which is part of AMF equipment stack).            203

Verify coil model/type by examining built-in coil fiducials.            204

Compare imaged implant with implants in the implant library to determine actual implant model.            205

Calculate difference between actual implant location in coordinate matrix with ideal location from simulation library (which includes model of verified transducer coil and implant image).  206

Calculate movement needed in, for example, rectilinear (x, y, z) or polar (r, theta, phi) coordinates to get to ideal location of transducer coil.            207

Manually reposition transducer coil per instructions given on AMF unit screen.            208

Automatically reposition coil using outputs generated by AMF unit.   209

SYSTEM FOR APPLICATION OF ALTERNATING MAGNETIC FIELDS TO REDUCE INFECTION

CROSS-REFERENCE TO RELATED APPLICATIONS

This application is a § 371 national stage of international application PCT/US21/64285, filed Dec. 20, 2021, which claims priority to U.S. Provisional Patent Application No. 63/129,692 filed Dec. 23, 2020 and entitled "System For Application Of Alternating Magnetic Fields To Reduce Infection". The content of each of the above applications is hereby incorporated by reference.

BACKGROUND

Prosthetic joint replacement has become an effective and widespread medical treatment for aging and damaged joints. However, prosthetic joints (or, more broadly, metallic implants such as fracture plates, bone anchors, and the like) may be susceptible to infection due to the buildup of bacterial biofilm on the joint. It is estimated that between 1% and 5% of prosthetic joint replacement patients suffer from these types of infections. Prior methods of treating these infections include additional surgeries and administration of prescribed oral and/or intravenous (IV) antibiotics. However, these treatments may not be completely effective and may require a high amount of resources.

An alternating magnetic field (AMF) is a non-invasive approach to treat infections of implanted medical devices, such as knee or hip implants. An external transducer coil generates time-varying AMF in the vicinity of a metal implant. The AMF generates surface electrical currents on the implant, which leads to heating largely restricted to the surface of the implant. In the case of an infected implant, bacteria (which may be in the form of a biofilm) adhere to the surface within this heated range. This localized surface interaction (including electrical currents and/or heating) can be used to eradicate pathogens or sensitize them to antimicrobial treatment.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIG. 2 is a method in an embodiment of the invention.

DETAILED DESCRIPTION

Figure 1:
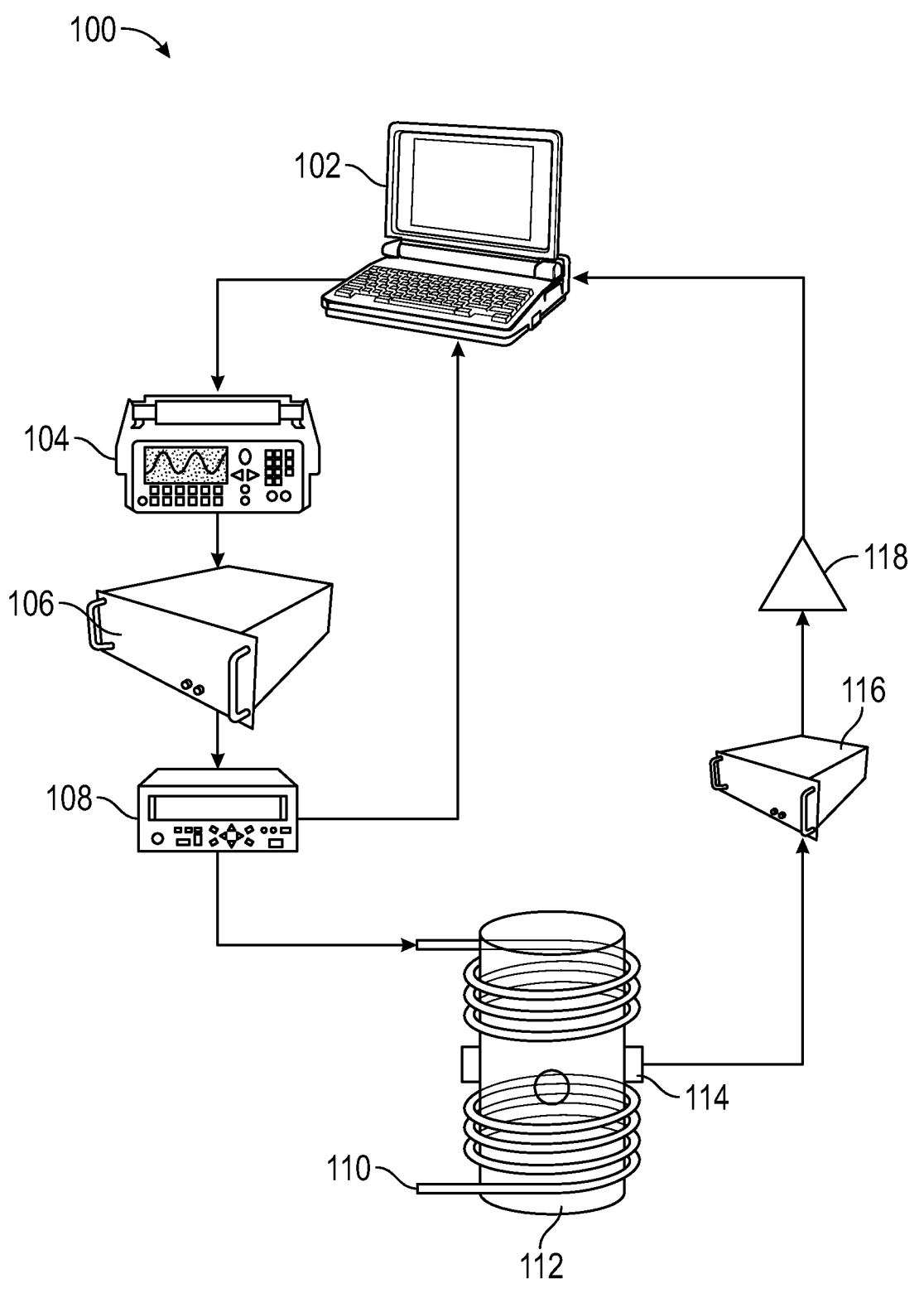
FIG. 1 is an AMF system in an embodiment of the invention.

Reference will now be made to the drawings wherein like structures may be provided with like suffix reference designations. In order to show the structures of various embodiments more clearly, the drawings included herein are diagrammatic representations of structures. Thus, the actual appearance of the fabricated structures, for example in a photo, may appear different while still incorporating the claimed structures of the illustrated embodiments (e.g., walls may not be exactly orthogonal to one another in actual fabricated devices). Moreover, the drawings may only show the structures useful to understand the illustrated embodiments. Additional structures known in the art may not have been included to maintain the clarity of the drawings. For example, not every layer of a device is necessarily shown. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact. Phrases such as "comprising at least one of A or B" include situations with A, B, or A and B.

Applicant determined precise positioning of the AMF transducer coil(s) outside of the patient and relative to the target metal implant within the patient is important for accurate surface interaction (e.g., heating) of the implant. Specifically, Applicant determined misalignment of the implant (i.e., incorrect positioning of the implant relative to the transducer coil(s)) can result in under or over exposure of the implant, which could impact the safety and efficacy of the treatment. User error and patient-to-patient variability need to be mitigated to achieve treatment within a safe envelope of operation. Because the implant is not visible in the non-invasive AMF treatment, Applicant determined a method and system is needed to ensure repeatable and precise positioning of the coil or coils with respect to the implant. In an embodiment, fiducial markers are integrated into the AMF transducer coil or coils such that the markers can be visualized on medical images (such as those taken by Computerized Tomography. MRI, or multi-planar X-Ray). Identification of these markers on medical images delivered to the AMF system display may be used (as described below) to produce precise parameters for localization of the coil(s) with respect to the implant.

A more detailed discussion of various embodiments now follows.

In an embodiment, AMF treatment transducer coils incorporate fiducial markers at predetermined locations inside of or in the proximity to the transducer coil windings or transducer housing such that these distinct markings may be visualized on commonly used medical imaging modalities (e.g., CT, XR, MRI).

Multiplanar or projection medical images with the desired fiducials visible may be sent to and processed by an algorithm (e.g., a pattern matching algorithm or algorithms) that is executed locally via at least one processor incorporated into the AMF portable system or remotely via cloud computing). In an embodiment, this results in identification of the fiducials, determination of the relationship between the fiducials and the target implant, and a display of the necessary movements to the coil(s) for precise alignment with regard to the implant.

In multi-transducer coil treatments, the above-mentioned algorithm(s) may detect the spatial conformation of the individual transducer coils in relation to one another using image guided confirmation of fiducials. For systems with multiple coils the coils may be in a single housing, a system of housings coupled to one another so that they are positioned dependent on one another, or multiple housings that are not coupled to each other such that the system includes independent coils that may be positioned independently of each other.

Fiducial markers may be composed of gold, nitinol, zirconium oxide, fluid capsules or other materials visible with imaging. In addition, external tags or "stickers" may be used to aid in automated placement of the transducer in specific locations and/or along a track.

The movement of the coil(s) may be automated via multi-axis rotational arms attached to the AMF treatment transducer coil. Alternatively, the transducer coil(s) may be attached to the body using a brace or similar method with means to manually articulate the coil(s) relative to the implant provided. For example, the movement of the coil may be mechanical and conducted via a series of jack screws, clamps, or the like attaching the AMF treatment transducer coil(s) to an extender arm from the AMF portable system.

An embodiment makes precise localization of a target implant within the window of treatment by AMF a seamless, integrated, and safe process. Incorporating fiducial markers into the coil design and employing medical image analysis algorithms (e.g., pattern matching) allows for precise adjustments of the AMF treatment transducer coil at the bedside.

In an embodiment, one or more images are acquired of the transducer coil, implant, and fiducials such that the 3D spatial position and orientation of the coil and implant relative to each other can be determined. The images are analyzed either manually (e.g., an algorithm that requires manual intervention, such as human identification of fiducials on a user interface) or automatically (e.g., automatic identification of fiducials) to calculate the necessary translation and rotation of the transducer coil(s) such that a desired relative position between the coil(s) and implant is achieved.

In multi-coil treatment sessions where coils of different sizes and shapes are utilized to generate the desired AMF, precise spatial confirmation of coils may be important for patient safety. Embodiments provide direct communication and recognition of AMF transducer coils via fiducial signatures to enable inter-treatment spatial movement in relation to the implant.

Thus, embodiments differ from conventional systems such as those that attempt to determine the position of an implant relative to the body/skeleton of person in which implant resides. Instead, embodiments determine the relative position of two objects (the implant inside the body and the coil outside the body) and provide the necessary repositioning information to achieve a desired relative position between the implant and coil. Further, embodiments differ from conventional systems such as those that rely on an internal implanted magnetic field detector to determine the position of the implant. Further, embodiments differ from conventional systems such as those that require a magnetic implant (which is used to, for example, position a catheter internally).

FIG. 1 depicts an exemplary control feedback system 100 for applying a surface interaction (e.g., inductive heating) to a foreign metallic implant according to an embodiment. In the embodiment shown, a desired treatment regimen may be selected and controlled by one or more control computers 102. The control computer 102 may be capable of transmitting control signals via one or more function generators 104, one or more amplifiers 106, and one or more power meters 108 to one or more AMF transmitters 110 (also referred to herein as coils) to control characteristics such as power, duty cycle, frequency, pulse duration, and pulse repetition frequency, among others. In the embodiment shown of control system 100, the control computer 102 may also be capable of receiving and processing sensory data (e.g., acoustic emissions) from the implant or tissue in its immediate vicinity through one or more remote sensors 114 to provide therapeutic feedback to system 102. In some embodiments, the control computer 102 may include a display to provide information about the progress of treatment to a user, as well as various input elements that may enable the user to interact with the control computer 102 and set desired parameters and/or adjustments. The control computer 102 may include standard components of a computer system such as a hard drive, monitor, printer, keyboard, mouse, among others, that may enable the user to interact with the control computer 102 and to record and/or reproduce data.

The control computer 102 may issue one or more commands or instructions to the function generator 104, which may produce a time varying electrical signal. The function generator 104 may have the ability to adjust the amplitude, frequency, phase offset, pulse duration and pulse repetition frequency of the time varying electrical signal. The function generator 104 may be controlled by the control computer 102 through elements such as a serial port, USB port, or Ethernet port, among others. In some embodiments, the function generator 104 may be directly integrated into the control computer 102. The time varying electrical signal may be amplified to a desired power level by the amplifier 106. In some embodiments, amplifier 106 may include a matching and tank circuit to achieve efficient power transfer and to tune the matching and tank circuit to a particular resonant frequency. The signal output of amplifier 106 may pass through the power meter 108, which may measure the forward and reflected power of the signal. This measurement data may be sent back to the control computer 102. The control computer 102 may use these measurements to adjust the levels of electrical power provided by the time varying electrical signal and/or monitor the efficiency of power transfer. If the control computer 102 adjusts the signal, it may issue an updated command to the function generator 104 to adjust the signal, which may then be transmitted through the amplifier 106 and power meter 108 for an updated measurement.

The signal emitted from the power meter 108 may be input into one or more AMF transmitters 110. In the embodiment shown, the AMF transmitter 110 may produce a time-varying magnetic field in a body area 112 to generate a surface interaction (e.g., heating) of the surface of a foreign metallic implant (not shown) located in the body area 112. One or more remote sensors 114 may be placed around the body area 112 being treated (e.g., heated). In some embodiments, the one or more remote sensors 114 may be placed directly on the surface of skin covering the body area 112. The one or more remote sensors 114 may be placed at desired intervals around the body area 112 being treated (e.g., heated). In some embodiments, the one or more remote sensors 114 may be placed at a distance above the body area 112. In some embodiments, the sensors may be temperature sensors, optical sensors, and/or wireless sensors. In some embodiments, the sensors may be removable sensors while in other embodiments, the sensors may be implanted in the body area 112 in various ways commonly known in the art. The sensory data may be converted to one or more signals by the sensors 114 and may be amplified by a pre-amplifier 116. The pre-amplifier 116 may transmit the one or more amplified signals to an analog-to-digital converter (ADC) 118, which may digitize the one or more amplified signals. In some embodiments, various types of data acquisition modules may be used. The one or more signals may then be input into and processed by the control computer 102 in order to determine whether adjustments to the time varying electrical signal are necessary.

FIG. 1 depicts an exemplary single coil AMF transmitter 110 according to an embodiment of the disclosure. A general type of transmitter can be some type of electrical conductor carrying a time-varying electrical signal located outside the patient's body. AMF transmitter 110 may be able to create a time varying magnetic field that crosses through a target metal implant in the body. A transmitter may comprise a solenoid. Because a solenoid may produce a uniform magnetic field along its inner axis, it may be suitable for exposing limbs and/or extremities to alternating magnetic fields. In other embodiments, a transmitter may comprise a saddle coil. A saddle coil may be placed around a hip to provide alternating magnetic fields for the treatment of implants in the pelvis. In other embodiments, multiple coils, a moving coil, and other types of AMF transmitters such as a pancake coil, among others, may be used to achieve a spatiotemporal variation of the alternating magnetic field.

The embodiment of FIG. 1 may be adapted for different shapes and sizes of foreign metallic implants as well as those located both superficially and deeply within the body. However, a sufficient magnetic field strength should be experienced by the implant to generate enough current flow to produce a desired temperature elevation. This may be achieved through the type of transmitter located outside the body and may make it likely that a different shape of transmitter may be optimal for different anatomical targets. For example, a solenoid may be well-suited for targeting objects within limbs and/or extremities, a saddle coil may be optimal for shoulders and hips, and an alternative type of AMF transmitter such as a pancake coil may be optimal for abdominal and/or vertebral targets.

FIG. 2 includes a method (200) in an embodiment. This method concerns an alignment problem whereby both the transducer coil and the implant are dynamic—the AMF system does not know the exact location of either the coil(s) or the implant. FIG. 2 is now discussed using an example of a medical technician treating implants for two different patients.

A first patient (Patient1) presents with a first implant (Kneeimplant1). The lab technician positions and stabilizes the knee and then positions the transducer coil as closely as possible over Patient1's knee. (Block 201) The technician then uses standard imaging technology (e.g., "C-arm") or similar to image the Transducer Coil (w/fiducials built-in) together with the implant (Kneeimplant1). (Block 202) A digitized version of the image from block 202 above is imported to the AMF system and placed in a coordinate system (e.g., 3D cartesian coordinate system). (Block 203) Unlike some conventional systems that use one coordinate system for a magnet (e.g., magnetic probe) and another coordinate system for a camera, the present embodiment uses a single (unified) representation in 3D space of both the transducer coil and the implant.

The fiducials on the imported model of the transducer coil are compared with a library having a finite set of transducer coil models (e.g., 20-30 models) stored in memory coupled to at least one processor of the AMF system. This may be used to verify the model of the transducer coil (via, e.g., pattern matching against the fiducials) that has been entered by the operator (Block 204), as well as establish the specific location of the transducer coil.

An embodiment includes a library (stored local or remote to the AMF system) having a collection of implants that have been verified for use with the specific transducer coil verified in Block 204. In some embodiments, the image of the implant from block 202 will be matched (e.g., pattern matching) by comparing it with images from the library of implant images. Once the correct implant model is determined (e.g., through pattern matching) that model is compared to the list of implants verified for use with the confirmed transducer coil. (Block 205)

In an embodiment the list of each verified implant includes location data for the required relative position of the verified transducer coil compared with a specific implant. The AMF system compares this location data to the location data calculated from the imported image in Block 203. The AMF system then calculates the difference in locations (Block 206). This difference is used to calculate the movement of the transducer coil needed to make it match the location data from Block 206 above in, for example, Cartesian (x, y, z) or polar (r, theta, phi) coordinates (Block 207). In an embodiment, this movement data is communicated to the operator via the display of the AMF system to enable manual repositioning of the transducer coil (Block 208). For example, this may be done by showing an image of the implant and the coil on the display, along with the magnitude and direction of motion required for desired alignment or orientation of the implant with respect to the coil. This motion can be detected by multiple methods, including, for example, position encoders in the arm which mounts the transducer coil. In other embodiments, the movement data is used to automatically reposition the transducer coil using what amounts to a robot arm. (Block 209).

Afterwards, the power, frequency, and timing of the AMF exposures may be controlled appropriately to achieve uniform surface interaction (e.g., heating) of the surface of the implant in as rapid a manner as possible under existing circumstances and technology. In order to accomplish uniform surface interaction (e.g., heating) of the implant while providing safety precautions to avoid damage to the surrounding tissue, a pulsed AMF exposure with appropriate delays may be applied from multiple AMF transmitters suitably arranged around the target implant. This process may be continued until a bacterial biofilm that may be present across the surface of an infected implant is weakened and/or eradicated to a desired extent.

This process may then be repeated for another patient (Patient2) presenting with a different implant (Hipimplant2). However, because Hipimplant2 is different form Kneeimplant1, the desired distance/orientation between the coil and hip implant differs from the desired distance/orientation between the coil and knee implant.

Figure 3:
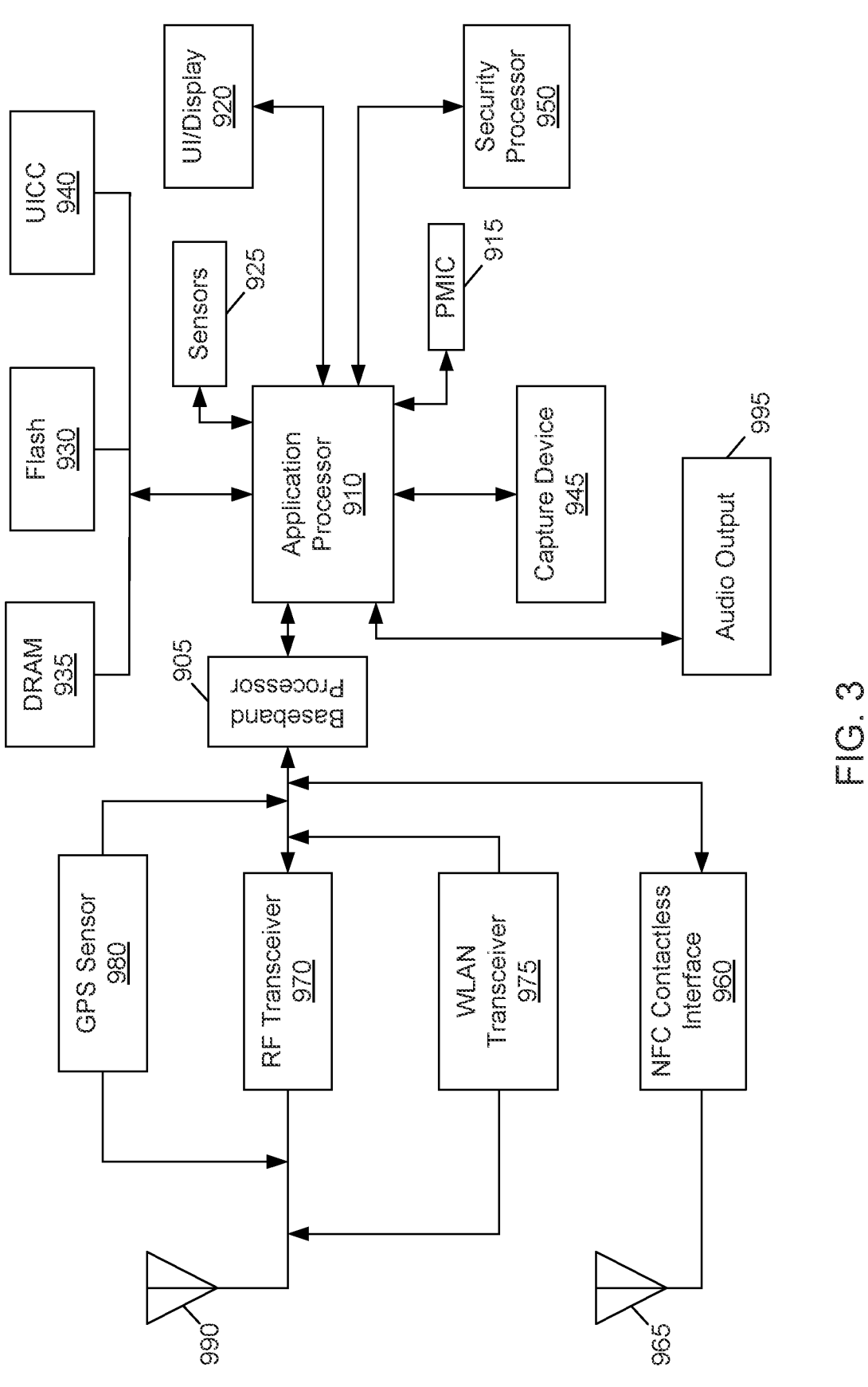
FIGS. 3, 4, and 5 include systems for use with various embodiments of the invention.

Referring now to FIG. 3, shown is a block diagram of an example system with which embodiments can be used. As seen, system 900 may be a smartphone or other wireless communicator or any other Internet of Things (IoT) device. A baseband processor 905 is configured to perform various signal processing with regard to communication signals to be transmitted from or received by the system. In turn, baseband processor 905 is coupled to an application processor 910, which may be a main CPU of the system to execute an operating system (OS) and other system software, in addition to user applications such as many well-known social media and multimedia apps. Application processor 910 may further be configured to perform a variety of other computing operations for the device. For example, it may also be used to perform some or all of the computing operations of the AMF control computer 102 in FIG. 1.

In turn, application processor 910 can couple to a user interface/display 920 (e.g., touch screen display). In addition, application processor 910 may couple to a memory system including a non-volatile memory, namely a flash memory 930 and a system memory, namely a DRAM 935. As further seen, application processor 910 also couples to audio output 995 and a capture device 945 such as one or more image capture devices that can record video and/or still images. Such a capture device may even include a medical imaging system such as a magnetic resonance imaging (MRI) or fluoroscopy system.

A universal integrated circuit card (UICC) 940 comprises a subscriber identity module, which in some embodiments includes a secure storage to store secure user information. System 900 may further include a security processor 950 (e.g., Trusted Platform Module (TPM)) that may couple to application processor 910. A plurality of sensors 925, including one or more multi-axis accelerometers may couple to application processor 910 to enable input of a variety of sensed information such as motion and other environmental information. These sensors may include position sensors which indicate the position of the AMF treatment coil (110) in FIG. 1. In addition, one or more authentication devices may be used to receive, for example, user biometric input for use in authentication operations.

As further illustrated, a near field communication (NFC) contactless interface 960 is provided that communicates in an NFC near field via an NFC antenna 965. While separate antennae are shown, understand that in some implementations one antenna or a different set of antennae may be provided to enable various wireless functionalities.

A power management integrated circuit (PMIC) 915 couples to application processor 910 to perform platform level power management. To this end, PMIC 915 may issue power management requests to application processor 910 to enter certain low power states as desired. Furthermore, based on platform constraints, PMIC 915 may also control the power level of other components of system 900.

To enable communications to be transmitted and received such as in one or more IoT networks, various circuitry may be coupled between baseband processor 905 and an antenna 990. Specifically, a radio frequency (RF) transceiver 970 and a wireless local area network (WLAN) transceiver 975 may be present. In general, RF transceiver 970 may be used to receive and transmit wireless data and calls according to a given wireless communication protocol such as 3G or 4G wireless communication protocol such as in accordance with a code division multiple access (CDMA), global system for mobile communication (GSM), long term evolution (LTE) or other protocol. In addition, a GPS sensor 980 may be present, with location information being provided to security processor 950 for use as described herein when context information is to be used in a pairing process. Other wireless communications such as receipt or transmission of radio signals (e.g., AM/FM) and other signals may also be provided. In addition, via WLAN transceiver 975, local wireless communications, such as according to a Bluetooth™ or IEEE 802.11 standard can also be realized. The wireless data received can include the coil image with fiducials (e.g., see block 202 in FIG. 2), as well as implant models (e.g., see block 205 in FIG. 2).

Figure 4:
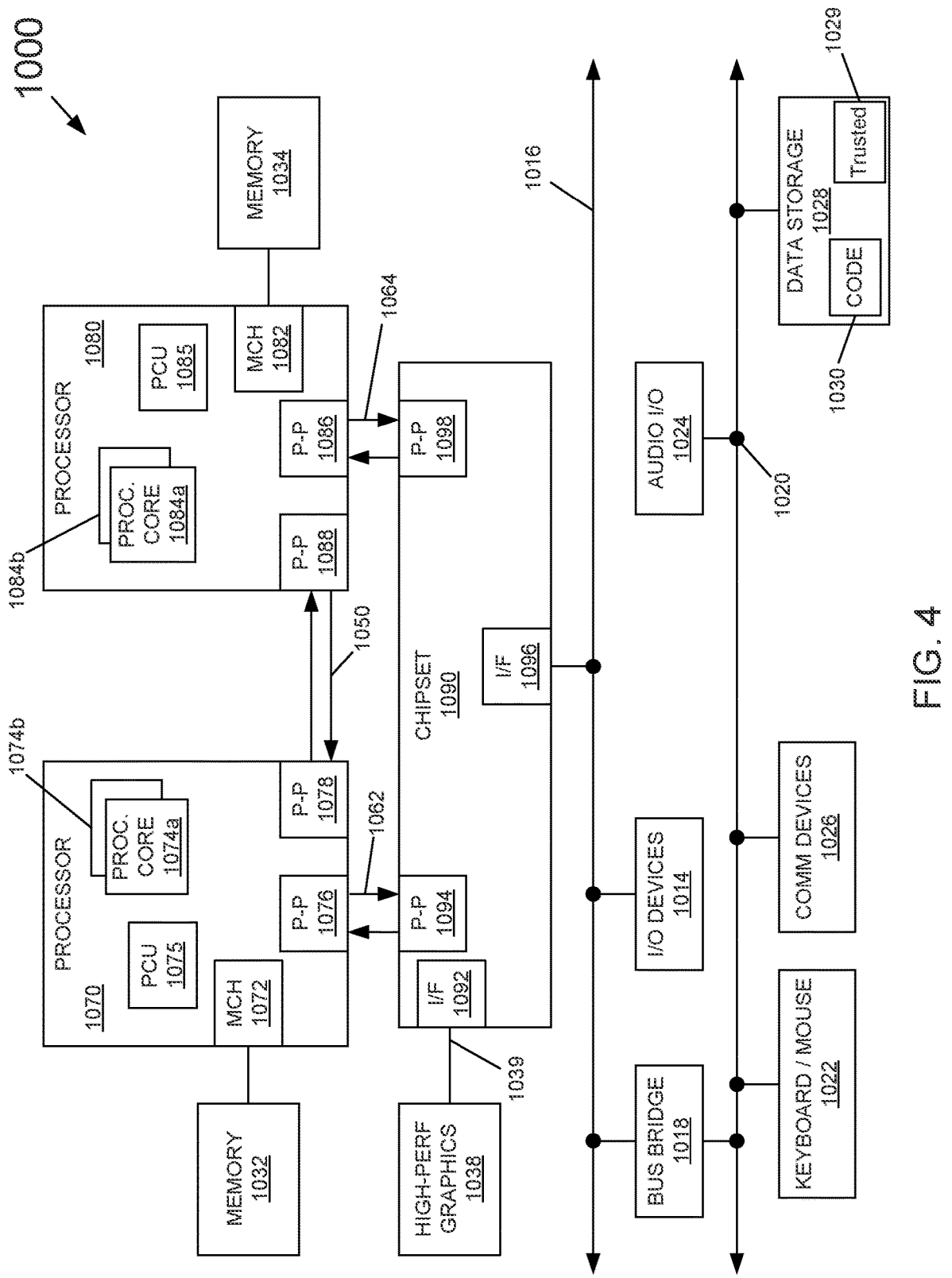

Referring now to FIG. 4, shown is a block diagram of a system in accordance with another embodiment of the present invention. Multiprocessor system 1000 is a point-to-point interconnect system such as a server system and includes a first processor 1070 and a second processor 1080 coupled via a point-to-point interconnect 1050. Each of processors 1070 and 1080 may be multicore processors such as SoCs, including first and second processor cores (i.e., processor cores 1074a and 1074b and processor cores 1084a and 1084b), although potentially many more cores may be present in the processors. In addition, processors 1070 and 1080 each may include a secure engine 1075 and 1085 to perform security operations such as attestations, IoT network onboarding or so forth.

First processor 1070 further includes a memory controller hub (MCH) 1072 and point-to-point (P-P) interfaces 1076 and 1078. Similarly, second processor 1080 includes a MCH 1082 and P-P interfaces 1086 and 1088. MCH's 1072 and 1082 couple the processors to respective memories, namely a memory 1032 and a memory 1034, which may be portions of main memory (e.g., a DRAM) locally attached to the respective processors. First processor 1070 and second processor 1080 may be coupled to a chipset 1090 via P-P interconnects 1062 and 1064, respectively. Chipset 1090 includes P-P interfaces 1094 and 1098.

Furthermore, chipset 1090 includes an interface 1092 to couple chipset 1090 with a high-performance graphics engine 1038, by a P-P interconnect 1039. In turn, chipset 1090 may be coupled to a first bus 1016 via an interface 1096. Various input/output (I/O) devices 1014 may be coupled to first bus 1016, along with a bus bridge 1018 which couples first bus 1016 to a second bus 1020. Various devices may be coupled to second bus 1020 including, for example, a keyboard/mouse 1022, communication devices 1026 and a data storage unit 1028 such as a non-volatile storage or other mass storage device. As seen, data storage unit 1028 may include code 1030, in one embodiment. As further seen, data storage unit 1028 also includes a trusted storage 1029 to store sensitive information to be protected. Further, an audio I/O 1024 may be coupled to second bus 1020.

Figure 5:
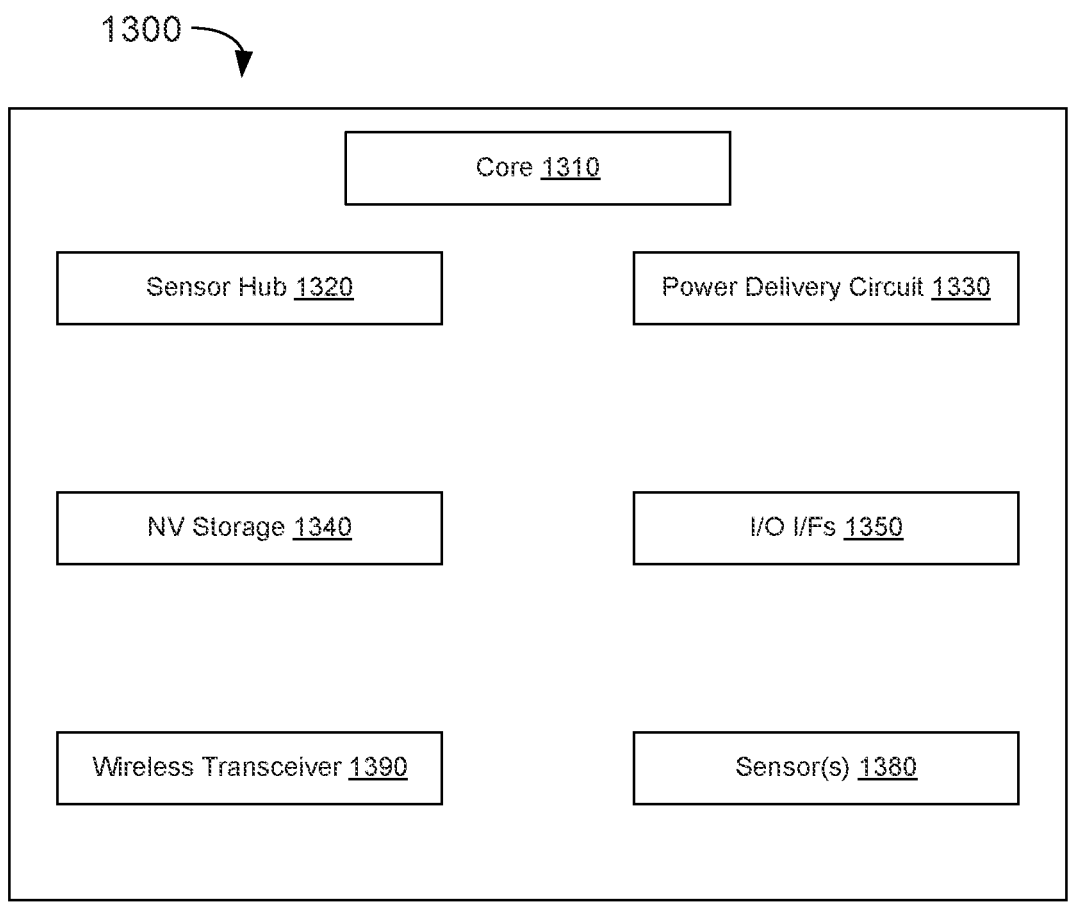

Referring now to FIG. 5, embodiments may be used in environments where IoT devices may include wearable devices or other small form factor IoT devices. Shown is a block diagram of a wearable module 1300 in accordance with another embodiment. In one particular implementation, module 1300 may be an Intel® Curie™ module that includes multiple components adapted within a single small module that can be implemented as all or part of a wearable device. As seen, module 1300 includes a core 1310 (of course in other embodiments more than one core may be present). Such core may be a relatively low complexity in-order core, such as based on an Intel Architecture® Quark™ design. In some embodiments, core 1310 may implement a Trusted Execution Environment (TEE). Core 1310 couples to various components including a sensor hub 1320, which may be configured to interact with a plurality of sensors 1380, such as one or more biometric, motion environmental or other sensors. A power delivery circuit 1330 is present, along with a non-volatile storage 1340. In an embodiment, this circuit may include a rechargeable battery and a recharging circuit, which may in one embodiment receive charging power wirelessly. One or more input/output (IO) interfaces 1350, such as one or more interfaces compatible with one or more of USB/SPI/I2C/GPIO protocols, may be present. In addition, a wireless transceiver 1390, which may be a Bluetooth™ low energy or other short-range wireless transceiver is present to enable wireless communications as described herein. In different implementations a wearable module can take many other forms.

Wearable and/or IoT devices have, in comparison with a typical general-purpose CPU or a GPU, a small form factor, low power requirements, limited instruction sets, relatively slow computation throughput, or any of the above.

Embodiments may be used in many different types of systems. For example, in one embodiment a communication device can be arranged to perform the various methods and techniques described herein. Such a system may also be used to perform some or all of the computing operations of the AMF control computer 102 in FIG. 1. Of course, the scope of the present invention is not limited to a communication device, and instead other embodiments can be directed to other types of apparatus for processing instructions, or one or more machine readable media including instructions that in response to being executed on a computing device, cause the device to carry out one or more of the methods and techniques described herein.

Program instructions may be used to cause a general-purpose or special purpose processing system that is programmed with the instructions to perform the operations described herein. Alternatively, the operations may be performed by specific hardware components that contain hardwired logic for performing the operations, or by any combination of programmed computer components and custom hardware components. The methods described herein may be provided as (a) a computer program product that may include one or more machine readable media having stored thereon instructions that may be used to program a processing system or other electronic device to perform the methods/operations or (b) at least one storage medium having instructions stored thereon for causing a system to perform the methods. The term "machine readable medium" or "storage medium" used herein shall include any medium that is capable of storing or encoding a sequence of instructions for execution by the machine and that cause the machine to perform any one of the methods described herein. The term "machine readable medium" or "storage medium" shall accordingly include, but not be limited to, memories such as solid-state memories, optical and magnetic disks, read-only memory (ROM), programmable ROM (PROM), erasable PROM (EPROM), electrically EPROM (EEPROM), a disk drive, a floppy disk, a compact disk ROM (CD-ROM), a digital versatile disk (DVD), flash memory, a magneto-optical disk, as well as more exotic mediums such as machine-accessible biological state preserving or signal preserving storage. A medium may include any mechanism for storing, transmitting, or receiving information in a form readable by a machine, and the medium may include a medium through which the program code may pass, such as antennas, optical fibers, communications interfaces, and the like. Program code may be transmitted in the form of packets, serial data, parallel data, and the like, and may be used in a compressed or encrypted format. Furthermore, it is common in the art to speak of software, in one form or another (e.g., program, procedure, process, application, module, logic, and so on) as taking an action or causing a result. Such expressions are merely a shorthand way of stating that the execution of the software by a processing system causes the processor to perform an action or produce a result.

A module as used herein refers to any hardware, software, firmware, or a combination thereof. Often module boundaries that are illustrated as separate commonly vary and potentially overlap. For example, a first and a second module may share hardware, software, firmware, or a combination thereof, while potentially retaining some independent hardware, software, or firmware. In one embodiment, use of the term logic includes hardware, such as transistors, registers, or other hardware, such as programmable logic devices. However, in another embodiment, logic also includes software or code integrated with hardware, such as firmware or micro-code.

The following examples pertain to further embodiments.

Example 1: A system comprising at least one alternating magnetic field (AMF) transmitter which includes a first coil and which is to apply AMF pulses to a first metallic implant via the first coil. The system includes at least one function generator, at least one processor, at least one input/output (I/O) port coupled to the at least one processor. Further, the system includes at least one machine-readable medium having stored thereon data which, if used by the at least one processor, causes the at least one processor to perform operations comprising: (1) pattern match a first portion of a first image to a library of metallic implant images (wherein the first portion of the first image depicts the first metallic implant); (2) pattern match a second portion of the first image to a library of coil images (wherein the second portion of the first image depicts a first coil); (3) determine a first orientation of the first and second portions of the first image with respect to one another. The first orientation is based on: (a) a first distance between the first and second portions of the first image with respect to one another, and (b) a first direction between the first and second portions of the first image with respect to one another. The operations further comprise: (1) selecting a first target orientation for the first metallic implant and the first coil with respect to one another from a library of target orientations between implants and coils; (2) determine a first difference between the first orientation and the first target orientation; and (3) output first reorientation instructions via the at least one I/O port in response to determining the first difference between the first orientation and the first target orientation.

A metallic implant may include prosthetic joints and/or various prosthetic implants such as pins, screws, rods, clamps, or foreign objects such as shrapnel. Any implant that is electrically conductive may also be included (for example, certain coatings of catheters or intravenous tubing).

Images, such as the "first image" image above may be imported to the system from a remote location. For instance, one or more servers in CountryA may be used to help better locate one or more coils located in CountryB with relation to one or more implants located in a patient present in CountryB.

Another version of claim 1. A system comprising: at least one alternating magnetic field (AMF) transmitter which includes a first coil and which is to apply AMF pulses to a first metallic implant via the first coil; at least one function generator; at least one processor; at least one input/output (I/O) port coupled to the at least one processor; and at least one machine-readable medium having stored thereon data which, if used by the at least one processor, causes the at least one processor to perform operations comprising: pattern match a first portion of a first image to a library of metallic implant images, wherein the first portion of the first image depicts the first metallic implant and a second portion of the first image depicts a first coil; determine a first orientation of the first and second portions of the first image with respect to one another, wherein the first orientation is based on: (a) a first distance between the first and second portions of the first image with respect to one another, and (b) a first direction between the first and second portions of the first image with respect to one another; select a first target orientation for the first metallic implant and the first coil with respect to one another from a library of target orientations between implants and coils; determine a first difference between the first orientation and the first target orientation; and output first reorientation instructions via the at least one I/O port in response to determining the first difference between the first orientation and the first target orientation.

Thus, "pattern match a second portion of the first image to a library of coil images, wherein the second portion of the first image depicts a first coil" is not necessarily included in all embodiments. In such an instance, the system may simply rely on the user's input that the proper type of coil has been identified.

Another version of example 1. A system comprising: at least one alternating magnetic field (AMF) transmitter which includes a first coil and which is to apply AMF pulses to a first metallic implant via the first coil; at least one function generator; at least one processor; at least one input/output (I/O) port coupled to the at least one processor; and at least one machine-readable medium having stored thereon data which, if used by the at least one processor, causes the at least one processor to perform operations comprising: pattern match a first portion of a first image to a library of metallic implant images, wherein the first portion of the first image depicts the first metallic implant; pattern match a second portion of the first image to a library of coil images based on fiducial markers of the first coil, wherein the second portion of the first image depicts a first coil; determine a first orientation of the first and second portions of the first image with respect to one another, wherein the first orientation is based on: (a) a first distance between the first and second portions of the first image with respect to one another, and (b) a first direction between the first and second portions of the first image with respect to one another; select a first target orientation for the first metallic implant and the first coil with respect to one another from a library of target orientations between implants and coils; determine a first difference between the first orientation and the first target orientation; and output first reorientation instructions via the at least one I/O port in response to determining the first difference between the first orientation and the first target orientation.

In this version of Example 1, pattern matching of the coil is based on fiducials of the coil. However, other embodiments may use pattern matching or coil identification using other techniques. Regarding "fiducials", an example of fiducials on a coil includes any stable metallic or X-Ray imageable feature with a defined (e.g., built into or on to the transducer) location (e.g., in Cartesian or polar coordinate space) that can be used to ascertain the location and alignment of the transducer coil assembly. An example of fiducials on an implant includes any specific imageable feature on the implant or an added metallic fiducial marker, typically used in radiology, which can be used to ascertain the location and alignment of the implant.

Another version of claim 1. A system comprising: at least one alternating magnetic field (AMF) transmitter which includes a first coil and which is to apply AMF pulses to a first metallic implant via the first coil; at least one function generator; at least one processor; at least one input/output (I/O) port coupled to the at least one processor; and at least one machine-readable medium having stored thereon data which, if used by the at least one processor, causes the at least one processor to perform operations comprising: determine a first orientation of first and second portions of a first image with respect to one another, wherein the first portion of the first image depicts a first metallic implant and the second portion of the first image depicts a first coil, wherein the first orientation is based on: (a) a first distance between the first and second portions of the first image with respect to one another, and (b) a first direction between the first and second portions of the first image with respect to one another; select a first target orientation for the first metallic implant and the first coil with respect to one another from a library of target orientations between implants and coils; determine a first difference between the first orientation and the first target orientation; and output first reorientation instructions via the at least one I/O port in response to determining the first difference between the first orientation and the first target orientation.

Thus, in some embodiments pattern matching (regarding the implant and/or coil) is not included.

Example 2. The system of example 1, wherein the first reorientation instructions include instructions regarding a movement of the first coil that is required to better approximate the first target orientation for the first metallic implant and the first coil with respect to one another.

These instructions may include code with which a system may automatically reorient coils and the like. However, these instructions may also include text and the like which communicates with a technician such that the technician knows to, for example, slide a coil three notches along a rail system, and the like.

Example 3. The system of example 2, wherein the first metallic implant is non-magnetic.

As used herein, "non-magnetic" means MRI-compatible as judged by persons of ordinary skill in the medical imaging art. Thus, the embodiment of Example 3 operates with implants that appropriate for passing through metal detectors in airports and the like. This is in contrast to, for example, vascular exploratory systems that use, for instance, an implantable magnetic probe or catheter which can be visualized as it navigates internally within a patient. Such systems would fail when used with non-magnetic implants (i.e., be unable to locate such implants).

Example 4. The system of example 3, wherein the first metallic implant includes less than 1% ferromagnetic materials.

Example 5. The system of example 4, wherein the first metallic implant includes less than 1% collectively of iron, nickel, cobalt, or combinations thereof.

Example 6. The system of example 3 wherein the first image simultaneously depicts the first metallic implant and the first coil.

As a result, a single image may be analyzed instead of a series of images. As a result, such a system may operate with more basic imaging systems and/or operate faster due to needing fewer images.

Example 7. The system of example 6 wherein the first metallic implant is one of a knee implant or a hip implant.

Thus, the system operates with typical implants that may be subject to biofilm accumulation. This is in contrast to exploratory probes/catheters located in patients for a relatively brief period of time.

Example 8. The system of example 7, wherein the operations comprise pattern matching the second portion of the first image to the library of coil images based on fiducial markers of the first coil.

Alternative version of Example 8. The system according to any of examples 1 to 7, wherein the operations comprise pattern matching the second portion of the first image to a library of coil images based on fiducial markers of the first coil.

Example 9. The system of example 8, wherein the first metallic implant includes no fiducial markers, because specific landmarks on known implants can act as fiducial markers.

Example 10. The system of example 9, wherein the operations comprise determining the first orientation of the first and second portions of the first image with respect to one another based on a three-dimensional (3D) Cartesian coordinate system.

For instance, this may be helpful in situations with more than one implant in the image.

Example 11. The system of example 9, wherein the operations comprise determining the first orientation of the first and second portions of the first image with respect to one another based on a three-dimensional (3D) space.

For instance, this may be helpful in situations with more than one implant.

Example 12. The system of example 11, wherein the operations comprise determining an identity of the first metallic implant in response to pattern matching the first portion of the first image to the library of metallic implant images.

Example 13. The system of example 12, wherein the operations comprise determining an identity of the first coil in response to pattern matching the second portion of the first image to the library of coil.

Example 14. The system of example 13, wherein the operations comprise determining whether the first coil and the first metallic implant are approved for operation with one another in response to determining the identities of the first coil and the first metallic implant.

For instance, an implant such as a metal plate for a finger may not be suitable for use with a saddle coil because the coil may be not be focused enough for a small plate and would unnecessarily target tissue beyond the plate. In such an instance, the system may keep an inexperienced technician from making a mistake. Such a system may at least alert the technician to the issue before eventually allowing the user to override the system's alarm.

Example 15. The system of example 14, wherein the operations comprise: (1) receiving user input via the at least one I/O port; (2) determining an additional identity of the first coil in response to receiving the user input; (3) comparing the additional identity of the first coil received via the user input with the identity of the first coil determined in response to pattern matching the second portion of the first image to the library of coils; (4) determining whether first coil and the first metallic implant are approved for operation with one another in response to comparing the additional identity of the first coil with the identity of the first coil.

Example 16. The system of example 15, wherein the operations comprise selecting the first target orientation for the first metallic implant and the first coil with respect to one another from the library of target orientations between implants and coils in response to determining the identities of the first coil and the first metallic implant.

Example 17. The system of example 16, wherein the operations comprise: (1) pattern matching a first portion of a second image to the library of metallic implant images, wherein the first portion of the second image depicts a second metallic implant; (2) pattern matching a second portion of the second image to the library of coil images, wherein the second portion of the second image depicts the first coil; (3) determine a second orientation of the first and second portions of the second image with respect to one another, wherein the second orientation is based on: (a) a second distance between the first and second portions of the second image with respect to one another, and (b) a second direction between the first and second portions of the second image with respect to one another; (4) select a second target orientation for the second metallic implant and the first coil with respect to one another from the library of target orientations between implants and coils; (5) determine a second difference between the second orientation and the second target orientation; and (6) output second reorientation instructions via the at least one I/O port in response to determining the second difference between the second orientation and the second target orientation.

This example is similar to Example 1 but addresses how the same coil may be used on two different implants. If the implants are differently constructed, shaped, sized, or implanted in different anatomic locations, the same coil may have a different desired orientation with the two implants.

Example 18. The system of example 17, wherein: (1) the first metallic implant has first profile, the first profile having a first shape and a first size; (2) the second metallic implant has a second profile, the second profile having a second shape and a second size; (3) the first profile is unequal to the second profile; (4) the first target orientation is unequal to the second target orientation in response to the first profile being unequal to the second profile.

In other words, the desired orientation between coil and implant may vary as a function of implant parameters such as profile, implant location, implant material composition, and the like.

Example 19. The system of example 16, wherein the operations comprise: (1) pattern matching a first portion of a second image to the library of metallic implant images, wherein the first portion of the second image depicts a second metallic implant; (2) pattern matching a second portion of the second image to the library of coil images, wherein the second portion of the second image depicts a second coil; (3) determine a second orientation of the first and second portions of the second image with respect to one another, wherein the second orientation is based on: (a) a second distance between the first and second portions of the second image with respect to one another, and (b) a second direction between the first and second portions of the second image with respect to one another; (4) select a second target orientation for the second metallic implant and the second coil with respect to one another from the library of target orientations between implants and coils; (5) determine a second difference between the second orientation and the second target orientation; and (6) output second reorientation instructions via the at least one I/O port in response to determining the second difference between the second orientation and the second target orientation.

Example 19 is similar to Example 17 but instead the coils are changed as well. Any combination of a change in coil (e.g., saddle coil vs. simple wound coil) and/or implant (e.g., profile, size, implant material composition, implant location (e.g., within an obese patient or a small child) may result in different desired orientations between coil or coils and implant or implants.

Example 20. The system of example 19, wherein: (1) the first metallic implant has first profile, the first profile having a first shape and a first size; (2) the second metallic implant has a second profile, the second profile having a second shape and a second size; (3) the first profile is unequal to the second profile; (4) the first target orientation is unequal to the second target orientation in response to the first profile being unequal to the second profile.

Example 21. The system of example 16, wherein the operations comprise: (1) pattern matching a first portion of a second image to the library of metallic implant images, wherein the first portion of the second image depicts the first metallic implant; (2) pattern matching a second portion of the second image to the library of coil images, wherein the second portion of the second image depicts a second coil; (3) determine a second orientation of the first and second portions of the second image with respect to one another, wherein the second orientation is based on: (a) a second distance between the first and second portions of the second image with respect to one another, and (b) a second direction between the first and second portions of the second image with respect to one another; (4) select a second target orientation for the first metallic implant and the second coil with respect to one another from the library of target orientations between implants and coils; (5) determine a second difference between the second orientation and the second target orientation; and (6) output second reorientation instructions via the at least one I/O port in response to determining the second difference between the second orientation and the second target orientation.

Example 21 is similar to Example 17 but instead the implant remains the same but the coils are changed. Any combination of a change in coil (e.g., saddle coil vs. simple wound coil) and/or implant (e.g., profile, size, implant material composition, implant location (e.g., within an obese patient or a small child) may result in different desired orientations between coil or coils and implant or implants.

Example 22. The system of example 21, wherein: the first coil has first profile, the first profile having a first shape and a first size; the second coil has a second profile, the second profile having a second shape and a second size; the first profile is unequal to the second profile; the first target orientation is unequal to the second target orientation in response to the first profile being unequal to the second profile.

Example 23. The system of example 16, wherein the operations comprise pattern matching the first portion of the first image to the library of metallic implant images based on at least one of probabilistic classification, feature selection, clustering, ensemble learning, multilinear subspace learning, real-valued sequence labeling, regression, sequence labeling, or combinations thereof.

Example 24. The at least one machine readable medium of any one of examples 1 to 23.

Thus, some embodiments may include software for performing operations but no hardware such as a coil, transmitter, function generator, processor, and the like.

Example 25. The at least one processor and the at least one machine readable medium of any one of examples 1 to 23.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a side of a substrate is the "top" surface of that substrate; the substrate may actually be in any orientation so that a "top" side of a substrate may be lower than the "bottom" side in a standard terrestrial frame of reference and still fall within the meaning of the term "top." The term "on" as used herein (including in the claims) does not indicate that a first layer "on" a second layer is directly on and in immediate contact with the second layer unless such is specifically stated; there may be a third layer or other structure between the first layer and the second layer on the first layer. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. A system comprising:
at least one alternating magnetic field (AMF) transmitter which includes a first coil and which is to apply AMF pulses to a first metallic implant via the first coil;
at least one function generator;
at least one processor;
at least one input/output (I/O) port coupled to the at least one processor; and
at least one machine-readable medium having stored thereon data which, if used by the at least one processor, causes the at least one processor to perform operations comprising:
pattern match a first portion of a first image to a library of metallic implant images, wherein the first portion of the first image depicts the first metallic implant and a second portion of the first image depicts the first coil;
determine a first orientation of the first and second portions of the first image with respect to one another, wherein the first orientation is based on: (a) a first distance between the first and second portions of the first image with respect to one another, and (b) a first direction between the first and second portions of the first image with respect to one another;
select a first target orientation for the first metallic implant and the first coil with respect to one another from a library of target orientations between implants and coils;
determine a first difference between the first orientation and the first target orientation; and
output first reorientation instructions via the at least one I/O port in response to determining the first difference between the first orientation and the first target orientation.

2. The system of claim 1, wherein the first reorientation instructions include instructions regarding a movement of the first coil that is required to better approximate the first target orientation for the first metallic implant and the first coil with respect to one another.

3. The system according to claim 1, wherein the first metallic implant is non-magnetic.

4. The system of claim 3, wherein the first metallic implant includes less than 1% ferromagnetic materials.

5. The system of claim 4, wherein the first metallic implant includes less than 1% collectively of iron, nickel, cobalt, or combinations thereof.

6. The system according to claim 1 wherein the first image simultaneously depicts the first metallic implant and the first coil.

7. The system according to claim 1 wherein the first metallic implant is one of a knee implant or a hip implant.

8. The system according to claim 1, wherein the operations comprise pattern matching the second portion of the first image to a library of coil images.

9. The system of claim 8, wherein the first metallic implant includes no fiducial markers.

10. The system of claim 8, wherein the operations comprise determining an identity of the first coil in response to pattern matching the second portion of the first image to the library of coil.

11. The system according to claim 10, wherein the operations comprise:

determining an identity of the first metallic implant in response to pattern matching the first portion of the first image to the library of metallic implant images;

determining whether the first coil and the first metallic implant are approved for operation with one another in response to determining the identities of the first coil and the first metallic implant.

12. The system of claim 11, wherein the operations comprise:

receiving user input via the at least one I/O port;

determining an additional identity of the first coil in response to receiving the user input;

comparing the additional identity of the first coil received via the user input with the identity of the first coil determined in response to pattern matching the second portion of the first image to the library of coils;

determining whether first coil and the first metallic implant are approved for operation with one another in response to comparing the additional identity of the first coil with the identity of the first coil.

13. The system of claim 12, wherein the operations comprise selecting the first target orientation for the first metallic implant and the first coil with respect to one another from the library of target orientations between implants and coils in response to determining the identities of the first coil and the first metallic implant.

14. The system according to claim 1, wherein the operations comprise determining the first orientation of the first and second portions of the first image with respect to one another based on a three-dimensional (3D) Cartesian coordinate system.

15. The system according to claim 1, wherein the operations comprise determining the first orientation of the first and second portions of the first image with respect to one another based on a three-dimensional (3D) space.

16. The system according to claim 1, wherein the operations comprise determining an identity of the first metallic implant in response to pattern matching the first portion of the first image to the library of metallic implant images.

17. The system according to claim 1, wherein the operations comprise:

pattern matching a first portion of a second image to the library of metallic implant images, wherein the first portion of the second image depicts a second metallic implant;

pattern matching a second portion of the second image to the library of coil images, wherein the second portion of the second image depicts the first coil;

determine a second orientation of the first and second portions of the second image with respect to one another, wherein the second orientation is based on: (a) a second distance between the first and second portions of the second image with respect to one another, and (b) a second direction between the first and second portions of the second image with respect to one another;

select a second target orientation for the second metallic implant and the first coil with respect to one another from the library of target orientations between implants and coils;

determine a second difference between the second orientation and the second target orientation; and output second reorientation instructions via the at least one I/O port in response to determining the second difference between the second orientation and the second target orientation.

18. The system of claim 17, wherein:

the first metallic implant has first profile, the first profile having a first shape and a first size;

the second metallic implant has a second profile, the second profile having a second shape and a second size;

the first profile is unequal to the second profile;

the first target orientation is unequal to the second target orientation in response to the first profile being unequal to the second profile.

19. The system according to claim 1, wherein the operations comprise:

pattern matching a first portion of a second image to the library of metallic implant images, wherein the first portion of the second image depicts a second metallic implant;

pattern matching a second portion of the second image to the library of coil images, wherein the second portion of the second image depicts a second coil;

determine a second orientation of the first and second portions of the second image with respect to one another, wherein the second orientation is based on: (a) a second distance between the first and second portions of the second image with respect to one another, and (b) a second direction between the first and second portions of the second image with respect to one another;

select a second target orientation for the second metallic implant and the second coil with respect to one another from the library of target orientations between implants and coils;

determine a second difference between the second orientation and the second target orientation; and output second reorientation instructions via the at least one I/O port in response to determining the second difference between the second orientation and the second target orientation.

20. The system of claim 19, wherein:

the first metallic implant has first profile, the first profile having a first shape and a first size;

the second metallic implant has a second profile, the second profile having a second shape and a second size;

the first profile is unequal to the second profile;

the first target orientation is unequal to the second target orientation in response to the first profile being unequal to the second profile.

21. The system according to claim 1, wherein the operations comprise:

pattern matching a first portion of a second image to the library of metallic implant images, wherein the first portion of the second image depicts the first metallic implant;

pattern matching a second portion of the second image to the library of coil images, wherein the second portion of the second image depicts a second coil;

determine a second orientation of the first and second portions of the second image with respect to one another, wherein the second orientation is based on: (a) a second distance between the first and second portions of the second image with respect to one another, and (b) a second direction between the first and second portions of the second image with respect to one another;

select a second target orientation for the first metallic implant and the second coil with respect to one another from the library of target orientations between implants and coils;

determine a second difference between the second orientation and the second target orientation; and output second reorientation instructions via the at least one I/O port in response to determining the second difference between the second orientation and the second target orientation.

22. The system of claim 21, wherein:

the first coil has first profile, the first profile having a first shape and a first size;

the second coil has a second profile, the second profile having a second shape and a second size;

the first profile is unequal to the second profile;

the first target orientation is unequal to the second target orientation in response to the first profile being unequal to the second profile.

23. The system according to claim 1, wherein the operations comprise pattern matching the first portion of the first image to the library of metallic implant images based on at least one of probabilistic classification, feature selection, clustering, ensemble learning, multilinear subspace learning, real-valued sequence labeling, regression, sequence labeling, or combinations thereof.

\* \* \* \* \*